United States Patent [19]

Wass

[11] Patent Number: 4,664,107
[45] Date of Patent: May 12, 1987

[54] INHALATION ACTIVATABLE DISPENSERS

[75] Inventor: Anthony C. L. Wass, Stamford, United Kingdom

[73] Assignee: Minnesota Mining and Manufacturing Company, St. Paul, Minn.

[21] Appl. No.: 709,316

[22] PCT Filed: Oct. 25, 1984

[86] PCT No.: PCT/US84/01721
§ 371 Date: Oct. 25, 1984
§ 102(e) Date: Dec. 17, 1984

[87] PCT Pub. No.: WO85/01880
PCT Pub. Date: May 9, 1985

[30] Foreign Application Priority Data

Oct. 28, 1983 [GB] United Kingdom ............... 8328808

[51] Int. Cl.⁴ ............................................. A61M 15/00
[52] U.S. Cl. ........................... 128/200.23; 128/203.15; 604/58
[58] Field of Search ...................... 128/200.23, 203.15; 604/58; 222/402.11, 402.12, 402.2

[56] References Cited

U.S. PATENT DOCUMENTS

| 3,187,748 | 6/1965 | Mitchell et al. | 128/173 |
| 3,456,644 | 7/1969 | Thiel | 128/173 |
| 3,456,645 | 7/1969 | Brock | 128/173 |
| 3,456,646 | 7/1969 | Phillips et al. | 128/173 |
| 3,565,070 | 2/1971 | Hanson et al. | 128/173 |
| 3,598,294 | 8/1971 | Hedrick et al. | 222/402.2 |
| 3,605,738 | 9/1971 | Ciranna | 128/173 |
| 3,636,949 | 1/1972 | Kropp | 128/173 |
| 3,732,864 | 5/1973 | Thompson et al. | 128/173 |
| 3,789,843 | 2/1974 | Armstrong et al. | 128/173 |
| 3,814,297 | 6/1974 | Warren | 222/402.13 |

FOREIGN PATENT DOCUMENTS

| 3040641 | 5/1982 | Fed. Rep. of Germany . |
| 2069300 | 9/1971 | France . |
| 1269554 | 4/1972 | United Kingdom . |
| 1335378 | 10/1973 | United Kingdom . |
| 1392192 | 4/1975 | United Kingdom . |
| 2061116 | 5/1981 | United Kingdom . |

Primary Examiner—Henry J. Recla
Attorney, Agent, or Firm—Donald M. Sell; James A. Smith; William L. Huebsch

[57] ABSTRACT

An inhalation activatable dispenser for use with an aerosol container in which a latch mechanism releasing vane is pivotably mounted in an air passage between an aerosol outlet valve and a mouthpiece, and the latch mechanism cannot be released if force to activate the dispenser is not applied before a patient inhales.

6 Claims, 15 Drawing Figures

INHALATION ACTIVATABLE DISPENSERS

TECHNICAL FIELD

This invention relates to inhalation activatable dispensers for use with aerosol container assemblies which contain medicaments for inhalation therapy, are pressurized with liquid propellants, and include a metering valve through which a series of metered medicament doses can be dispensed.

BACKGROUND ART

Inhalation activatable dispensers for use with aerosol container assemblies of the type described above are well known, their general purpose being to afford proper coordination of the dispensing of a dose of medicament with the inhalation of the patient to allow the maximum proportion of the dose of medicament to be drawn into the patient's bronchial passages. Examples of such dispensers are described in British Patent Specification Nos. 1,269,554, 1,335,378, 1,392,192 and 2,061,116 and U.S. Pat. Nos. 3,456,644, 3,456,645, 3,456,646, 3,565,070, 3,598,294, 3,814,297, 3,605,738, 3,732,864, 3,636,949, 3,789,843 and 3,187,748.

DISCLOSURE OF THE INVENTION

The present invention provides a new and improved inhalation activatable dispenser which is more simple and difficult to misuse than known prior art dispensers.

According to the present invention, there is provided an inhalation activatable dispenser for use with an aerosol container assembly including a metering valve for dispensing medicament from a container included in the assembly, which valve includes a hollow stem which is movable relative to the rest of the valve and the container between an outer closed position to which the stem is biased by a valve spring, and an inner position at which a metered dose of medicament is dispensed from the valve through the stem. The dispenser has a housing formed with a through air passage terminating at a mouthpiece. The housing is adapted to receive the container assembly with the stem in a support block with a through orifice communicating with the air passage and affords the application of a force sufficient to move the valve stem to its inner discharge position in opposition to the valve spring. A latch mechanism is provided comprising a vane disposed in the air passage and movable upon inhalation at the mouthpiece from a blocking position across the air passage at which the latch mechanism is engaged and prevents relative movement between the container and support block in response to the force, and a non-blocking position at one side of the air passage at which the latch mechanism affords such movement in response to the force. The dispenser is operable to dispense aerosol into the air passage by the sequential operations of: applying such a force when the vane is in its blocking position; and inhaling at the mouthpiece, causing movement of the vane to its non-blocking position which releases the lock mechanism and allows the force to move the stem relative to the container to dispense aerosol into the air passage for inhalation by the user.

In the present invention the vane is pivotally mounted in the air passage between the orifice and the mouthpiece. Such location of the vane allows the dispenser to have a small overall size, allows an air inlet for the air passage to be located close to the mouthpiece so that the air inlet and mouthpiece can be closed by a single cover, and separates the container and any moving parts other than the vane from the air passage to minimize the chances of foreign matter being inhaled. Also this position of the vane affords the use of locking means such as a projection on the mouthpiece cover to positively restrain movement of the vane when the dispenser is not in use.

Also in the present invention the latch mechanism includes means which prevent its release to dispense a dose of medicament into the air passage when the vane is in its non-blocking position prior to the application of the force in the dispenser. Thus, it is ensured that the patient cannot commence inhalation too soon before the dose is dispensed and thereby draw an inadequate proportion of the dose into the bronchial passages. Dispensing of a dose only occurs upon inhalation if the force is first applied in the apparatus; however, if the patient inhales first, so that the vane is moved to its non-blocking position, the subsequent application of the force will be inoperable to dispense a dose.

The force to operate the dispenser may be provided by manually pressing the container into the housing of the dispenser or alternatively may be provided by a spring which is manually compressed prior to inhalation through the device to provide a predetermined force to make the apparatus ready for operation by such inhalation.

BRIEF DESCRIPTION OF DRAWING

The invention will be more thoroughly described with reference to the accompanying drawing wherein like reference numerals refer to like parts in the several views and wherein.

DETAILED DESCRIPTION

Referring now to FIGS. 1 through 7 there is shown a first embodiment of an inhalation activatable dispenser according to the present invention generally designated by the reference numeral 20.

Figure 1:
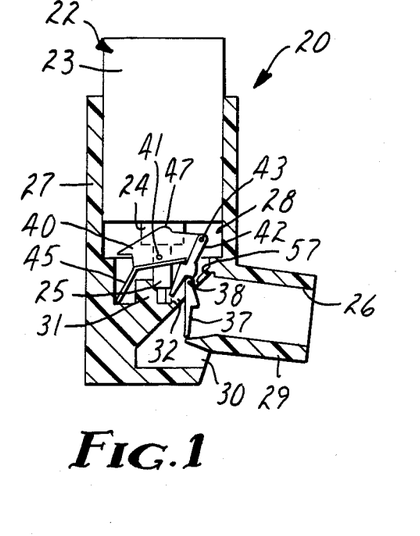
FIG. 1 is a sectional view of a first embodiment of an inhalation activatable dispenser according to the present invention.
Figure 2:
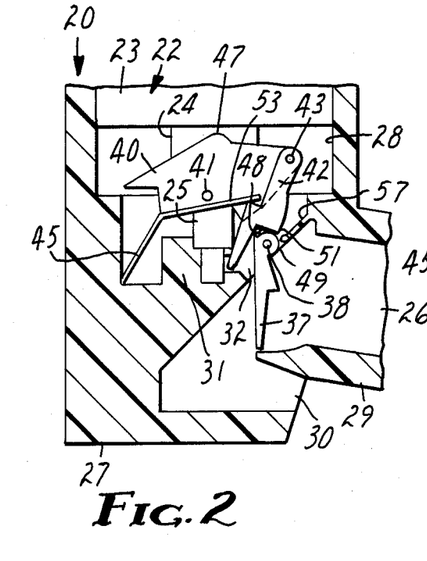
FIGS. 2 through 7 are enlarged fragmentary sectional views showing the operational sequence of the dispenser of FIG. 1 with FIGS. 6 and 7 having a catch in the dispenser broken away to show detail.

As is best seen in FIG. 1, the dispenser 20 is adapted for use with an aerosol container assembly 22 of the known kind including a container 23 containing a medicament and liquid propellant, and a metering valve 24 (such as described in U.S. Pat. No. 3,598,294 incorporated herein by reference) fixed in one end of the container 23 for dispensing a metered dose of the medicament from the container 23 through a hollow stem 25 included in the valve 24. The stem 25 is movable relative to the container 23 between an outer charging position (to which the stem 25 is biased by a spring in the valve 24) and an inner discharging position at which a metered dose is discharged through the stem 25.

The dispenser 20 comprises a housing 27 defining an open ended chamber 28 into which the container assembly 22 may be inserted stem 25 down, a mouthpiece 29, and a through air passage 26 extending from an inlet opening 30 adjacent the mouthpiece 29 to an outlet through the mouthpiece 29. The housing includes a nozzle block 31 having a socket adapted to receive the stem 25, and a through orifice 32 adapted to direct medicament and liquid propellant from the stem 25 into the air passageway 26. Thus upon manual movement of the container 23 toward the block 31 the stem 25 will be moved to its discharging position relative to the container 23 so that medicament is discharged through the orifice 32 into the air passageway 26 toward the mouthpiece for inhalation by the patient. To prevent any escape of the medicament and propellant upwardly out of the nozzle block 31, and to accommodate a certain variation in sizes of stems 25, the dispenser 20 may include a soft seal gasket (not shown) located in the nozzle block 31.

In order to coordinate the dispensing of the medicament with the inhalation of a patient, the dispenser is provided with a latch mechanism including a vane 37 mounted on the housing 27 for a pivotable movement about an axis 38 between a blocking position blocking a portion of the air passageway 26 between the orifice 32 in the nozzle block 31 and the mouthpiece 29 (FIGS. 1, 2 and 3) and a non-blocking position (FIGS. 5, 6 and 7) at one side of and not blocking the air passageway 26.

The latch mechanism also comprises a rocker 40 mounted on the housing 27 for pivotal movement about a fulcrum 41, and a catch 42 mounted on the rocker 40 for pivotal movement about an axis 43 spaced from the rocker fulcrum 41. When the dispenser 20 is not in use or in a normal condition (FIGS. 1 and 2) the container assembly 23 is spaced from the rocker 40 by the internal valve spring in the metering valve 24. The rocker 40 has an integrally formed spring 45 which normally positions the rocker 40 in an initial position at which the catch 42 is held over, but spaced from the vane 37.

Figure 3:
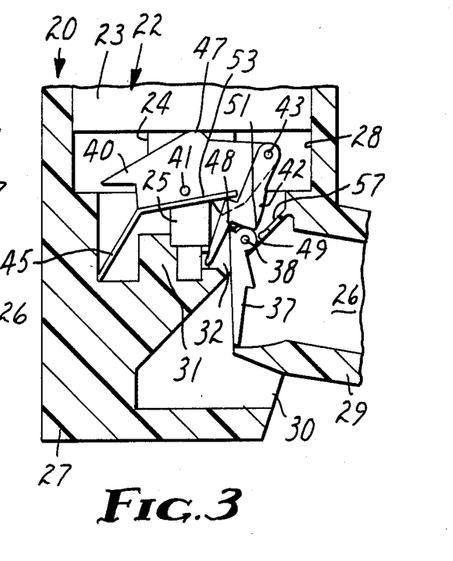

To operate the dispenser 20, a user first presses the container 23 into the chamber 28 in the housing 27 until the container 23 contacts the rocker 40 at a point 47 close to the fulcrum 41 and rotates the rocker 40 through a small angle about the fulcrum 41 to a retaining position at which further rotation of the rocker 40 or movement of the container 23 is prevented by the engagement between a shoulder 48 of the catch 42 and an edge surface 49 of the vane 37 to produce a cocked condition for the dispenser 20 (FIG. 3). The latch mechanism is then engaged to prevent further movement of the container 23 toward the nozzle block 31 by the applied force until inhalation by the user through the mouthpiece 29 moves the vane 37 from its blocking to its non-blocking position to release the latch mechanism and allow the container 23 to be further depressed relative to the stem 25 held in the block 31 to dispense a dose of medicament.

Figure 4:
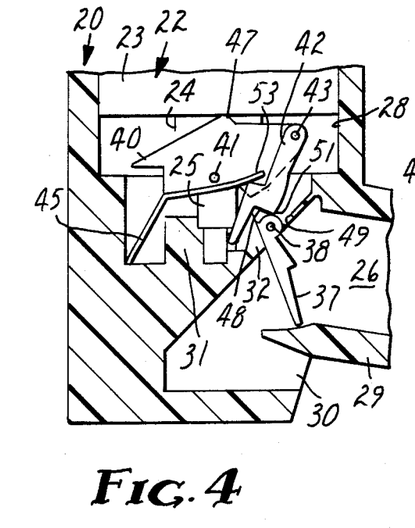
Figure 5:
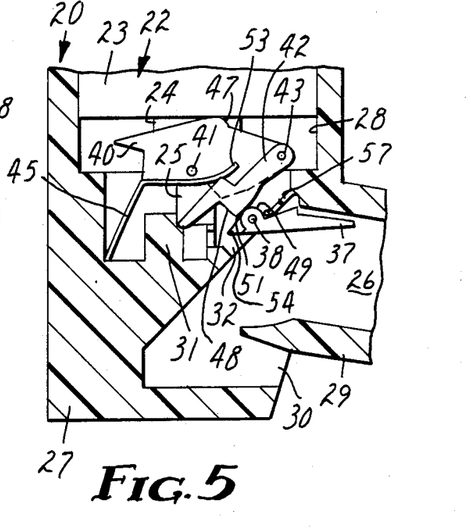
Figure 6:
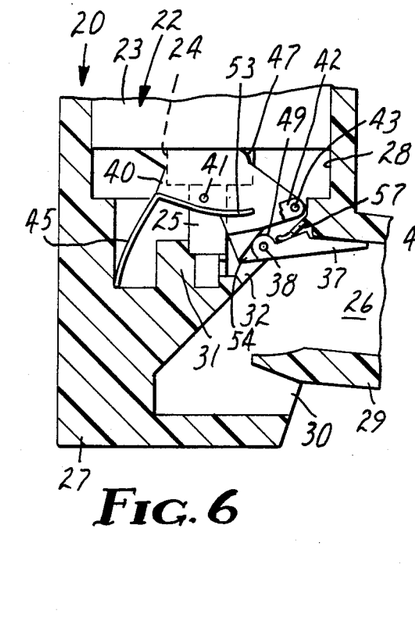
Figure 7:
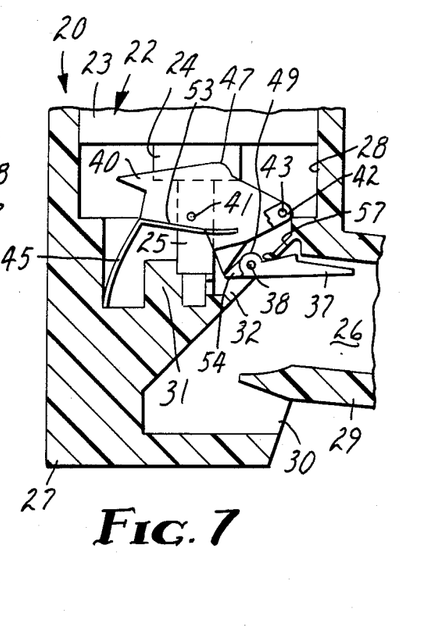

One position of the vane 37 and latch 42 in the latch mechanism during such inhalation is shown in FIG. 4. The vane 37 has begun to rotate counter-clockwise due to the reduced air pressure in front of it caused by the inhalation. The shoulder 48 on the catch 42 is a true arc about its pivot axis 43, and the edge surface 49 of the vane 37 is a true arc about its pivot axis 38 so that frictional contact between the edge surface 49 of the vane 37 and the shoulder 48 of the catch 42 causes the rotating vane 37 to pivot the catch 42 clockwise about its axis 43. Because both contact surfaces are true arcs, no pivotal movement of the rocker 40 can occur during this stage. The arcuate shoulder 48 of the catch 42, however, terminates at a heel 51. Once the heel 51 reaches a line between the axes 38 and 43, the latch mechanism can no longer prevent the downward movement of the container 23 due to the pressure applied by the user. The edge surface 49 of the vane 37 rotates onto and along a side contact surface of the catch 42 which is a true arc about the rocker fulcrum 41 since the rocker 40 carries a second spring 53 which then biases the catch 42 into contact with the vane 37 as the rocker 40 pivots further around the fulcrum 41 to a non-retaining position and allows the container 23 to move further into the chamber 28 to provide a dispense condition for the dispenser 20 (FIG. 6).

In order that movement of the container 23 into the chamber 28 will assist in lifting the vane 37, the vane 37 is provided with a pair of projecting ledges 54 that successively and respectively are engaged by the catch 42 and the rocker 40 to push the vane 37 fully to one side of the air passageway 26 and hold it clear of the air passage portion from orifice 32 to the mouthpiece 29. The metering valve 24 dispenses (FIG. 6) a metered dose of medicament during the final part of the downward movement of the container 23 and during an early part of the inhalation cycle of the user to ensure that a maximum portion of the dose enters the user's bronchial passages.

To avoid undue noise caused by the contact between the vane 37 and the housing 27, the movement of the vane 37 to its non-blocking position is damped by contact with a flexible web 57 integrally formed with the housing 27 and by the expulsion of air from a pocket defined between the web 57 and an adjacent face of the vane 37.

When the user releases the manual pressure on the container 23, it moves away from the nozzle block 31 under the influence of the internal valve spring. The rocker 40 is then free to rotate counter-clockwise to its normal position (FIG. 2) under the influence of the rocker spring 45. The vane 37 should then fall freely into a vertical position under the influence of gravity but, in the event that it adheres to the housing wall, a peg on the moving rocker 40 will engage an arm on the vane 37 to break such adhesion and allow the vane 37 to fall. The catch 42 is returned to the position shown in FIG. 2 by the action of the rocker spring 45, and the operating mechanism is now again in its normal condition, ready for a repeat of the dispensing operation.

The operating mechanism, as described above, is designed to ensure that the dose is delivered during the early part of the inhalation cycle. It also includes means for preventing incorrect use of the dispenser 20, such as by inhaling through the mouthpiece 29 before force is applied to press the container 23 into the housing 27, or by holding the dispenser 20 in an inverted position.

In the former case, inhalation will cause the vane 37 to move to its non-blocking position but without simultaneously pivoting the catch 42, since the catch 42 will only be pivotable if it has first been brought into contact with the vane 37 by the application of force to move the container 23. Once the vane 37 has fully moved to its non-blocking position, if the container 23 is subsequently depressed, no further counter-clockwise movement of the vane 37 is possible to rotate the catch 42. The catch 42 is then retained by the edge surface 49 of the vane 37 and the mechanism cannot be released so that no dose of medicament can be discharged.

In the latter case, holding the dispenser 20 in an inverted position is undesirable in that the metering valve 24 cannot be relied upon to dispense a full dose. The mechanism will not operate in the inverted position because the vane 37 will immediately fall under gravity into the same horizontal non-blocking position to which it is moved by inhalation. The latch mechanism will therefore be unable to be released for the same reason described above where inhalation occurs before force is applied to the container 23.

Figure 8:
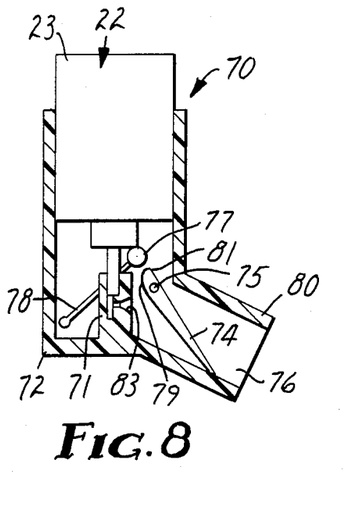
FIGS. 8 through 10 are sectional views of a second embodiment of an inhlation activatable dispenser according to the present invention showing the operational sequence of the dispenser.
Figure 9:
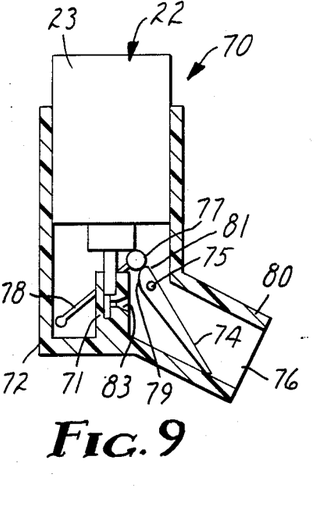
Figure 10:
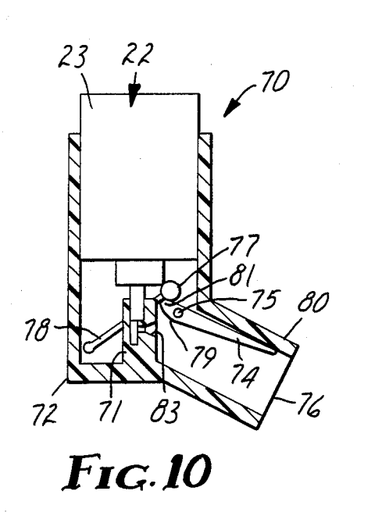

FIGS. 8, 9 and 10 illustrate an alternate construction for an inhalation activatable dispenser 70 according to the present invention for use with the container assembly 22 and which is operated in the same manner as the device 20, but in which a latch mechanism for resisting movement of the container 23 toward a nozzle block 71 on a housing 72 for the dispenser 70 comprises only a vane 74 pivotably mounted on the housing 72 about an axis 75 for movement between blocking and non-blocking positions corresponding in position and function to those of the vane 37 in the device 20, and a roller 77 rotatably carried at the end of an arm 78 pivotably mounted on the housing 72 at its end opposite the roller 77. With the vane 74 in its blocking position the roller 77 contacts a vane surface 79 which is circular about the axis 75 and is disposed so that pressure against the surface 79 caused by pressure against the opposite side of the roller 77 will cam the vane 74 to its non-blocking position and will prevent movement of the roller 77 out from under the container 23 (FIG. 8). Movement of the vane 74 to its non-blocking position upon inhalation through a mouthpiece 80 on the device 70, however, will cause the roller 77 to move around an end of the vane 74 and onto an edge surface 81 of the vane 74 that will allow the roller 77 to move along the edge surface 81 of the vane 74 and from beneath the container 23 end to allow the container 23 to move relative to the nozzle block 71 (FIG. 10) so that the valve assembly discharges a metered dose of medicament and propellant through an orifice 83 in the block 71 into the air passageway 76 toward the mouthpiece 80.

Figure 11:
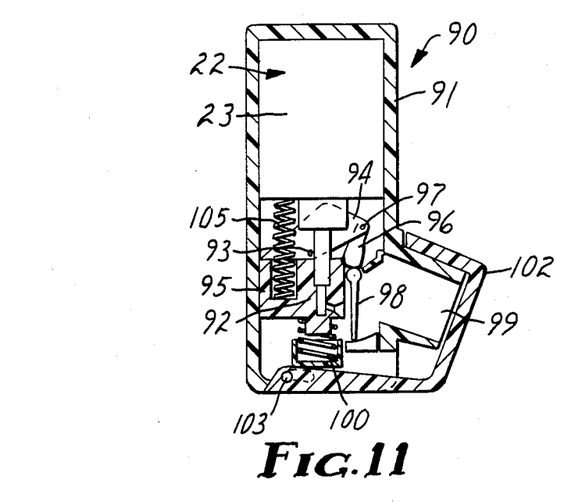
FIG. 11 is a sectional view of a third embodiment of an inhalation activatable dispenser according to the present invention shown with a cover on the device closed.
Figure 12:
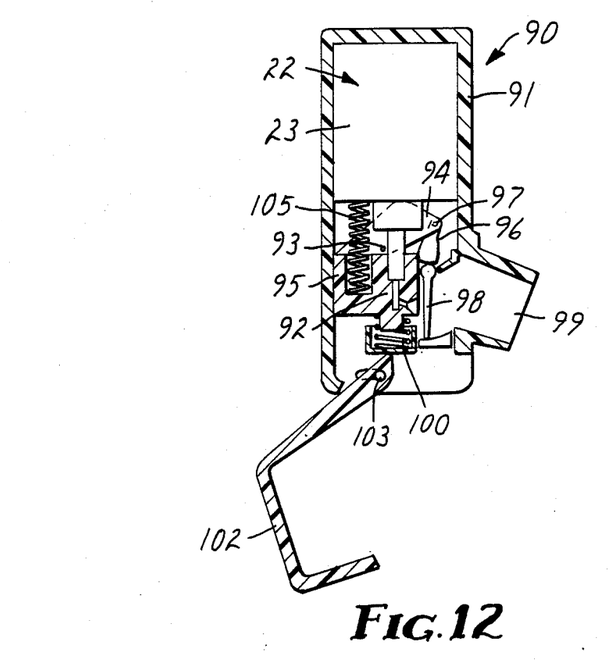
FIG. 12 is a sectional view of the device of FIG. 11 shown with the cover open.

While in the dispensers 20 and 70 the nozzle block 31 and fulcrum 41 for the rocker 40 are fixed on the housings 27 and 72 and the container 23 is movable within the housings 27 and 72 to produce discharge of a dose of medicament from the metering valve 24, it is also possible, as is illustrated in the dispenser embodiment 90 shown in FIGS. 11 and 12 to fix the container 23 within a housing 91 for the dispenser 90 and mount a nozzle block 92 and a fulcrum 93 for a rocker 94 similar to the rocker 40 on a member 95 which is movable relative to the rest of the housing 91. The use of a catch 96 similar to the catch 42 pivotably mounted at an axis 97 on the rocker 94 and a vane 98 similar to the vane 37 pivotably mounted on the housing 91 in a through air passageway 99 defined in the housing 91 then affords operation of the dispenser 90 in a manner similar to the operation of the dispenser 20 except that the force applied to operate the device 90 is applied to the member 95 centrally toward the container assembly 22 either manually, or, as illustrated, by a coil spring 100 that may be compressed by pivotal movement of a cover 102 for the device 90 from a closed position (FIG. 11) to an open position (FIG. 12) around a pin 103, which cover 102 and coil spring 100 arrangement has the advantage of being easily operable and providing a uniform force to drive the dispenser 90.

The device 90 as illustrated, may also include a second spring 105 as a supplement to the internal spring in the metering valve 24 to help hold the container assembly 22 and rocker 94 apart when the dispenser is in its normal position. This permits the accommodation by the dispenser of a wider range of nozzle stem lengths, and provides for a discernible degree of initial movement of the member 95 to the cocked position for the dispenser. The outward force exerted by this second spring will of course be sufficiently small to be overcome by the coil spring 100.

Figures 13, 14, 15:
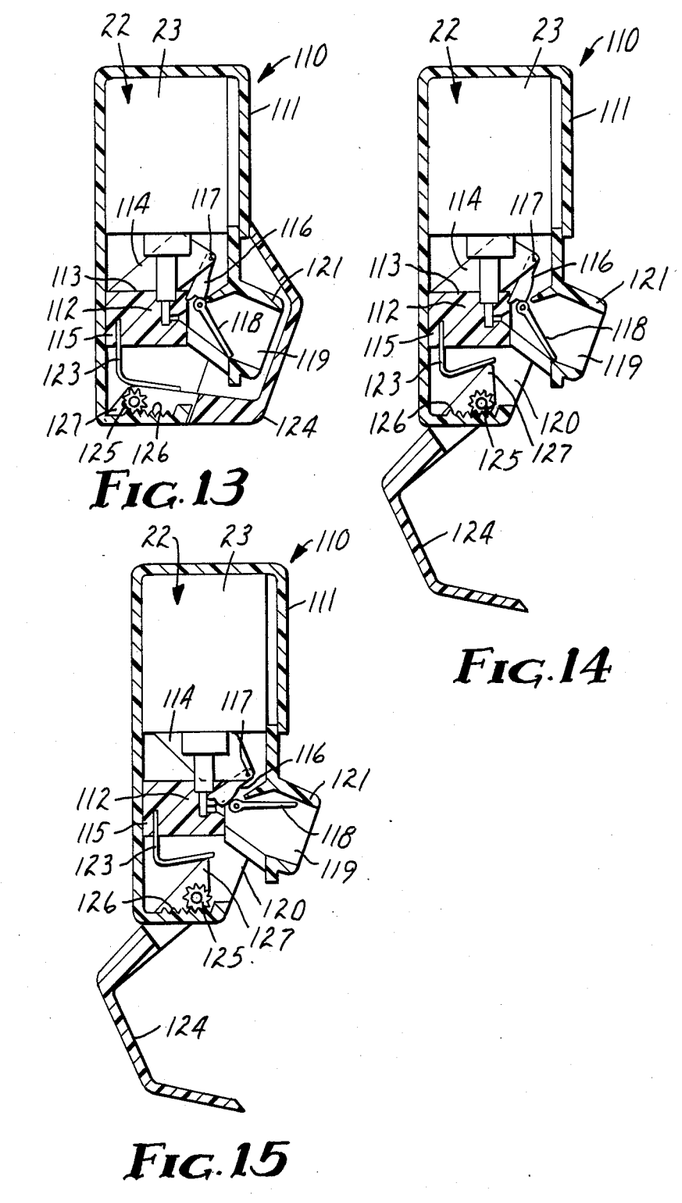
FIGS. 13, 14 and 15 are sectional views of a fourth embodiment of an inhalation activatable dispenser according to the present invention showing its operational sequence.

FIGS. 13, 14 and 15 illustrate an embodiment 110 of a dispenser according to the present invention which function like the dispenser 90, and like the dispenser 90 fixes the container 23 within a housing 111 for the dispenser 110 and mounts a nozzle block 112 and a fulcrum 113 for a rocker 114 similar to the rocker 40 on a member 115 which is movable relative to the rest of the housing 111. Also included are a catch 116 similar to the catch 42 pivotably mounted at an axis 117 on the rocker 114 and a vane 118 similar to the vane 37 pivotably mounted on the housing 111 in a through air passageway 119 defined in the housing 11 from an inlet 120 to a mouthpiece 121. Like the dispenser 90, the dispenser 110 operates in a manner similar to the operation of the dispenser 20 except that the force applied to operate the dispenser 110 is applied to the member 115 toward the container assembly 22 by an L-shaped leaf spring 123 that may be compressed by movement of a cover 124 for the device 90 from a closed position (FIG. 13) to an open position (FIG. 14). As illustrated, opening of the cover 124 causes a spur gear 125 fixed on the cover 124 to move along a rack 126 formed on the housing 111 so that a cam end 127 on the cover 124 engages and presses the spring 123 toward the container 23 to provide the force needed to operate the dispenser 110.

In any of the embodiments, provision may be made for the adjustment of the position of the catch at initial contact with the vane, whereby the degree of rotation of the vane required to roll the catch over the heel and thus permit the vial to fire may be varied. An adjuster in the form of a screw projecting through the nozzle block may be arranged to bear on the tail end of the catch whereby the initial angular position of the catch may be altered by varying the projecting length of the screw.

I claim:

1. An inhalation activatable dispenser for use with an aerosol container having a valve for dispensing aerosol from an outlet in the container, the valve having a hollow stem which is movable relative to the container between an outer closed position and an inner discharging position of the valve, said dispenser including a housing having a mouthpiece and an air passage therethrough terminating at said mouthpiece, the housing being adapted to receive such an aerosol container, having a support block with a socket adapted to receive said stem and a through orifice communicating between said socket and said air passage, and said dispenser including latch means having parts movable between an engaged position and a release position for preventing when said parts are in said engaged position the movement of said container and said support block toward each other upon the application of a force to bias the container and said support block toward each other and for affording when said parts are in said release position movement of said container and said support block toward each other in response to said force to move said stem to its inner discharge position, said parts of said latch means comprising a vane mounted on said housing in said air passageway between said orifice and said mouthpiece for movement toward said mouthpiece solely under the influence of inhalation through said mouthpiece from a blocking to a non-blocking position with respect to said passageway during the application of said force to move said parts from said engage to said release position so that inhaling at the mouthpiece causes movement of said vane to its non-blocking position which allows said force to move said stem relative to the container to its inner discharging position to dispense aerosol into the air passage for inhalation by the patient.

2. A dispenser according to claim 1 wherein said latch means includes means for preventing movement of said parts to said release position when said vane is in said non-blocking position prior to application of said force to bias the container and said support block toward each other.

3. A dispenser according to claim 1 wherein said vane is mounted on said housing for pivotal movement about an axis and has a drive surface forming an arc about said axis, the parts of said latch means further comprise a rocker mounted on said housing for pivotable movement about a fulcrum and a catch pivotably mounted on said rocker about a pivot axis remote from said fulcrum, said catch having a driven edge surface forming an arc about said pivot axis adapted to engage said arcuate drive surface on said vane, and a side surface disposed so that pivotal movement of said vane from said blocking to said non-blocking position during the application of said force causes frictional driving engagement of said drive surface with said driven surface to pivot said catch to afford movement of said side surface along said vane and pivoting of said rocker about said fulcrum to afford movement of said support block and container toward each other.

4. A dispenser according to claim 1 wherein said support block is fixed on said housing and said housing affords manual application of said force between said container and said housing.

5. A dispenser according to claim 1 wherein said container is fixed on said housing, said support block is fixed on a member movable with respect to said housing, and said dispenser comprises a spring adapted to be compressed and apply said force between said container and support block.

6. A dispenser according to claim 5 comprising a cover for said mouthpiece pivotably mounted on said housing and adapted to compress said spring upon movement of said cover from closed to an open position.

* * * * *

UNITED STATES PATENT AND TRADEMARK OFFICE
CERTIFICATE OF CORRECTION

PATENT NO. : 4,664,107

DATED : May 12, 1987

INVENTOR(S) : Anthony C. L. Wass

It is certified that error appears in the above-identified patent and that said Letters Patent is hereby corrected as shown below:

Page 1, Block 73, Assignee "Minnesota Mining and Manufacturing Company" should be -- Riker Laboratories, Inc. --.

Signed and Sealed this

Twenty-ninth Day of March, 1988

Attest:

DONALD J. QUIGG

*Attesting Officer*      *Commissioner of Patents and Trademarks*